US010633340B1

(12) United States Patent
Blumberg et al.

(10) Patent No.: US 10,633,340 B1
(45) Date of Patent: Apr. 28, 2020

(54) SYNTHESIS OF OXIME NERVE AGENT ANTIDOTES

(71) Applicant: Southwest Research Institute, San Antonio, TX (US)

(72) Inventors: Shawn T. Blumberg, San Antonio, TX (US); Antonio A Menchaca, Seguin, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 16/207,464

(22) Filed: Dec. 3, 2018

(51) Int. Cl.
*C07D 213/53* (2006.01)

(52) U.S. Cl.
CPC .................................. *C07D 213/53* (2013.01)

(58) Field of Classification Search
CPC . C07D 215/227; C07D 401/12; C07D 213/53
See application file for complete search history.

(56) References Cited

U.S. PATENT DOCUMENTS 4,948,912 A * 8/1990 Lyle, Jr. ................ C07C 205/57 546/266
8,404,850 B2 * 3/2013 Cabell .................. C07D 213/53 546/264

OTHER PUBLICATIONS

Environmental Protection Agency (EPA); Bis(chloromethyl)ether (BCME); 542-88-1; summary created in Apr. 1992; updated in Jan. 2000, 4 pgs. <<https://www.epa.gov/sites/production/files/2016-09/documents/bis-chloromethyl-ether>> accessed Nov. 18, 2018.
Eyer, P.; "The Role of Oximes in the Management of Organophosphorus Pesticide Poisoning"; Toxicology Review 2003; 22 (3); pp. 165-190.
The National Institute for Occupational Safety and Health (NIOSH), Appendix B—Thirteen OSHA-Regulated Carcinogens, 2016 Center for Disease Control (CDC) <<https://www.cdc.gov/niosh/ng/nengapdxv.html>>; accessed Feb. 19, 2019 (2 pgs).
Van Duuren, B.; "Comparison of Potency of Human Carcinogens: Vinyl Chloride, Chloromethylmethyl Ether and Bis (chloromethyl)ether"; Environmental Research 49, 1989, pp. 143-151.
Wilhelm, C., et al "A Comprehensive Evaluation of the Efficacy of Leading Oxime Therapies in Guinea Pigs Exposed to Organophosphorus Chemical Warfare Agents or Pesticides"; Toxicology and Applied Pharmacology 281 (2014) pp. 254-265.

* cited by examiner

*Primary Examiner* — D Margaret M Seaman
(74) *Attorney, Agent, or Firm* — Grossman, Tucker, Perreault & Pfleger, PLLC

(57) ABSTRACT

The present invention relates to a new route to bis-quaternary pyridinium oximes which can be utilized to restore activity of acetylcholinesterase inhibited by combination with organophosphates.

17 Claims, No Drawings

SYNTHESIS OF OXIME NERVE AGENT ANTIDOTES

FIELD

The present invention relates to a synthetic route to bis-quaternary pyridinium oximes which can be utilized to restore activity of acetylcholinesterase inhibited by combination with organophosphates.

BACKGROUND

Stimulating signals are typically carried by acetylcholine within a nervous system synapse. Such signals may be discontinued by a specific type of cholinesterase enzymes, acetylcholinesterase, which breaks down acetylcholine. If cholinesterase inhibiting chemicals are present, they may then prevent the breakdown of acetylcholine thereby disrupting normal nervous system activity. For example, certain chemical classes of pesticides, such as organophosphates and carbamates, may result in toxic cholinesterase inhibition. Accordingly, if an individual is regularly exposed to such inhibitors, there remains a need to prophylactically or therapeutically treat such toxicity. Among other things, individuals or animals who may have been exposed to a carbamate type cholinesterase inhibitor may currently be treated with atropine, and those exposed to organophosphates may beneficially be treated with a pralidoxime antidote.

Organophosphorous nerve agents (OPNA) have been used as chemical weapons, and as noted, in pesticides, have reportedly cause an estimated 300,000 deaths per year worldwide. See, e.g., Eyer, P. et al, *Toxicol. Rev.* 2003, 22, 165-90. Currently, the bis-pyridinium oximes known as: (1) HLo-7 dimethylsulfate (DMS), otherwise known as 1-[[[4-(aminocarbonyl)pyridinio]methoxy]methyl]-2,4-bis [(hydroxyimino)methyl]pyridinium dimethane sulfonate); (2) HI-6 DMS, otherwise known as (1-[[[4-(aminocarbonyl) pyridinio]methoxy]methyl]-2-[(hydroxyimino)methyl]pyridinium dimethane sulfonate); and (3) obidoxime DMS, otherwise known as oxo-[[1-[[4-(oxoazaniumylmethylidene)pyridin-1-yl]methoxymethyl]pyridin-4-ylidene] methyl]azanium dimethane sulfonate, are reportedly among the most effective reactivators of OPNA inhibited acetylcholinesterase (AChE).

However, current methods to synthesize the above referenced antidotes require the use of chemical compounds which are extremely toxic and which lead to relatively large amounts of side products that are difficult to remove from the reaction media. Accordingly, a continuing need exists for more efficient pathways to produced desired reactivators of OPNA inhibited AChE.

SUMMARY

A method of forming bis-quaternary pyridinium oximes comprising:

supplying benzoic anhydride having the following structure:

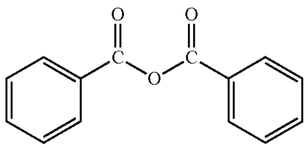 [SMILES: O=C(OC(=O)c1ccccc1)c1ccccc1]

reacting said benzoic anhydride with trioxane to form a dibenzoyloxymethyl ether having the following structure

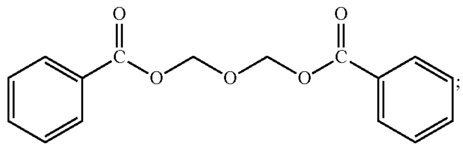 [SMILES: O=C(OCOCOC(=O)c1ccccc1)c1ccccc1]

;

supplying a substituted pyridine having the following structure:

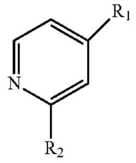

wherein $R_1$ and $R_2$ may be independently selected from the group consisting of hydrogen, alkyl, —CH═NOH or —$CONH_2$;

combining said dibenzyl acetoxymethyl ether with said substituted pyridine and forming a salt having the following structure:

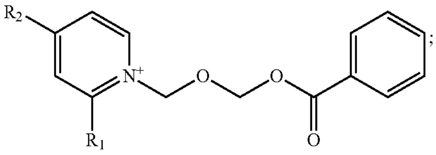

;

reacting said salt with a substituted pyridine having the following structure:

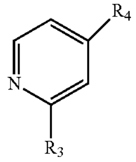

wherein $R_1$ and $R_2$ may be independently selected from the group consisting of hydrogen, alkyl group, —CH═NOH or —$CONH_2$;

and forming a bis-pyridinium aldoxime salt of the following structure:

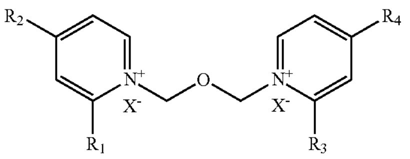

wherein $R_3$ and $R_4$ may be independently selected from the group consisting of consisting of hydrogen, alkyl, —CH═NOH or —$CONH_2$ and $X^-$ comprises Cl—, Br—, I— or $^-OSO_2CH_3$.

The present invention also relates to a therapeutic method of treating a person or animal for intoxication with a phosphorous containing cholinesterase inhibitor, comprising administering to a person or animal a bis-pyridinium aldoxime salt formed by the above method.

DETAILED DESCRIPTION

As noted above, current methods to synthesize HLo-7 DMS, HI-6 DMS and obidoxime DMS require use of chemical linkers such as bis(2-chloromethyl) ether (BCME) (2) or bis(2-methylsulfonoxymethyl) ether (BMME) (3), which are identified as extremely carcinogenic, with an exposure limit of 0.0003 ppm. In addition, BMME is relatively difficult to prepare and is unstable. Below is a summary of the relevant chemical reactions utilized employing such toxic reagents:

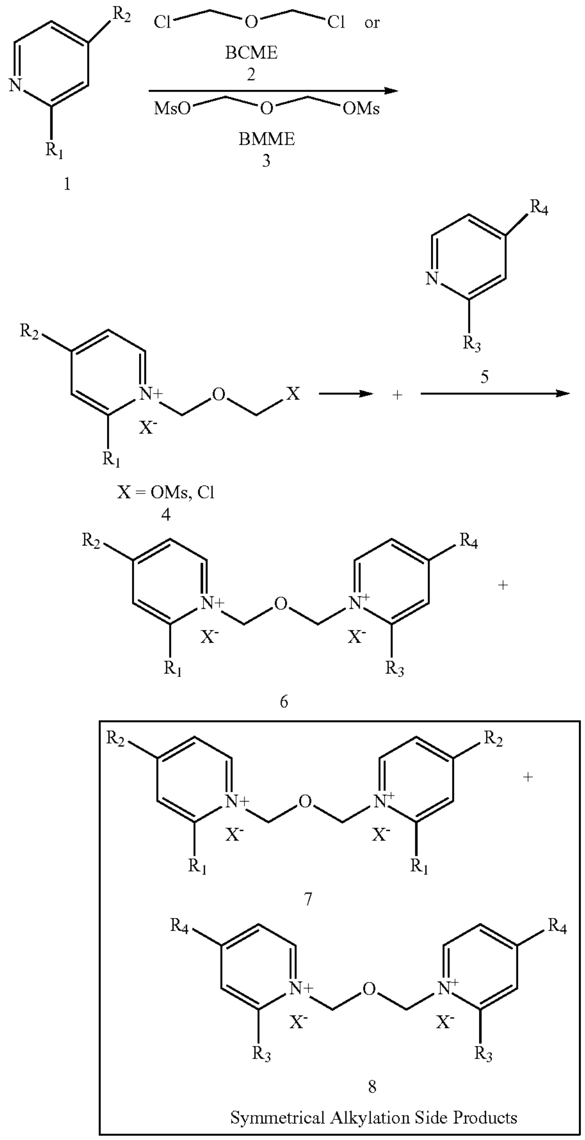

In the above scheme, $R_1$, $R_2$, $R_3$ and $R_4$ may be independently selected from the group consisting of hydrogen, alkyl, —CH═NOH or —$CONH_2$. Reference to —OMS is reference to —$OSO_2CH_3$. Reference to $X^-$ is therefore reference to the anionic form, either Cl—, Br—, I— or $^-OSO_2CH_3$. Accordingly, in compound 6, when $R_1$ is hydrogen, $R_2$ is —CH═NOH, and $R_3$ and $R_4$ are both —CH═NOH, and $X^-$ is $^-OSO_2CH_3$, the compound is HLo-7. When $R_1$=—CH═NOH, $R_2$ is hydrogen, R3 is hydrogen and $R_4$ is —CH═NOH, and $X^-$ is $^-OSO_2CH_3$, the compound is HI-6 DMS. When $R_1$ and $R_3$ are hydrogen, and $R_2$ and $R_4$ are —CH═NOH, and $X^-$ is $^-OSO_2CH_3$, the compound is obidoxime DMS. As can be seen from the above, aside from the use of relatively toxic reagents (BCME or BMME), these methods produce relatively large amounts of symmetrical side products 7 and 8, which are relatively difficult to remove from the desired oximes.

The present invention is directed at the formation of a dibenzoyloxymethyl ether 10 which can be formed by reacting compound 9, a benzoic anhydride, optionally containing one or more electron withdrawing groups (EWG) on each of the two aromatic rings, preferably in the ortho and/or para position with respect to the carbonyl functionality, with trioxane and $H_2SO_4$ as an acid catalyst. Preferably, each aromatic ring on compound 9 contains one or two electron withdrawing groups. Accordingly, the reaction occurs preferably in an organic solvent, such as dicholorethane (DCE), where the optional and preferred one or more EWG is illustrated on the reaction scheme below:

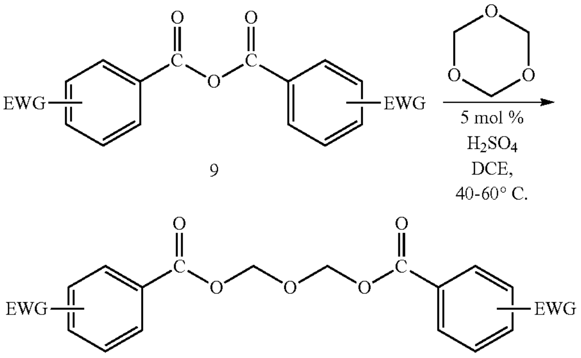

10

In the above, the optional electron withdrawing groups (EWG), if present, may be preferably and independently selected from an organic trihalide (—$CF_3$, —$CCl_3$), sulfonate (—$SO_3H$), nitro group (~$NO_2$), ammonium (—$NH_3$+), aldehyde (—CHO), ketones (—COR), carboxylic acid (—COOH), acyl chloride (—COCl), benzoate esters (—COOPh), amide (—$CONH_2$) or halides (—F, —Cl, —Br, —I). Preferably, the EWG is the same on each of the two aromatic rings.

The dibenzoyloxymethyl ether 10 can then provide a reactive species which can alkylate substituted pyridines such as compound 1 to form a salt 11:

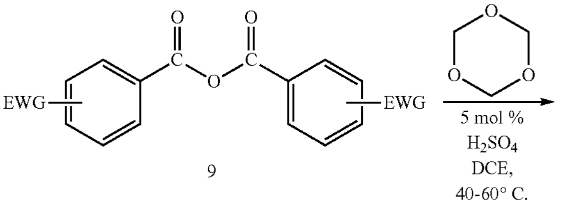

-continued

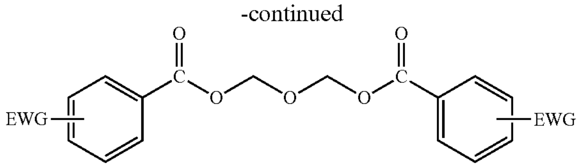

10

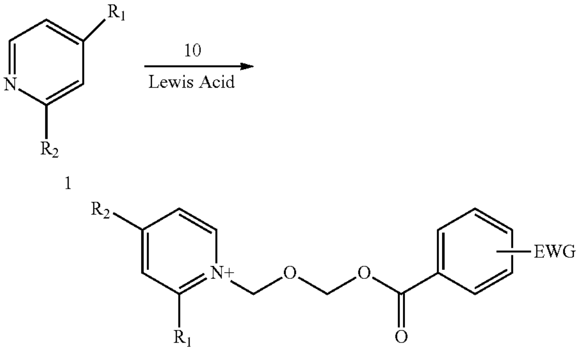

1

11

As illustrated below, when an additional Lewis acid and a second substituted pyridine such as compound 5 is added and reacted with compound 11 the desired bis-pyridinium OPNA antidotes 6 are formed at a yield in the range of 30-90%. Preferred Lewis acids include trimethylsilyl iodide (TMSI), Trimethylsilyloxytrifluoromethanesulfonate (TM-SOTf), $BF_3.OEt_2$ or Trimethylsilyloxymethanesulfonate (TMSOMs). It should be noted that in this synthetic scheme, $R_1$, $R_2$, $R_3$ and $R_4$ may be independently selected from the group consisting of hydrogen, alkyl, —CH═NOH or $—CONH_2$. In addition, to $X^-$ is again reference to the anionic form, either Cl—, Br—, I— or $^-OSO_2CH_3$. Reference to alkyl groups preferably include, e.g., methyl ($—CH_3$), ethyl ($—CH_2CH_3$), propyl ($—CH_2CH_2CH_3$) or butyl ($—CH_2CH_2CH_2CH_3$) groups.

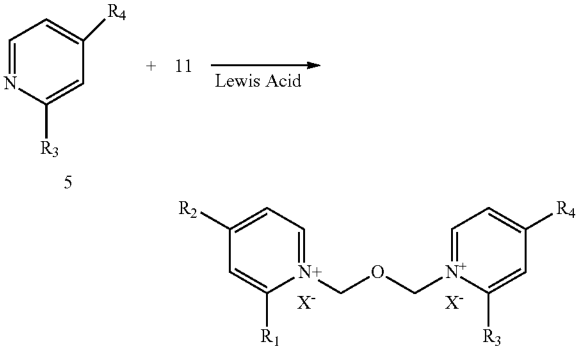

5

6

Accordingly, the present invention relates to a synthetic procedure for the formation of bis-quaternary pyridinium oximes which can be utilized to restore activity of acetylcholinesterase by combination with organophosphates. The procedure avoids the use of bis(2-chloromethyl) ether (BCME) (2) or bis(2-methylsulfonoxymethyl) ether (BMME) (3) as well as the formation of compounds 7 and 8 (symmetrical alkylation side products). Moreover, once prepared, the bis-quaternary pyridinium oximes may be readily incorporated into a pharmaceutically accepted carrier and administered in an antidotal amount to therapeutically treat exposure to a phosphorous containing cholinesterase inhibitor. A pharmaceutical accepted carrier may be understood herein as an aqueous formulation containing the bis-quaternary pyridinium oximes in the form of an aqueous solution, suspension or emulsion. The pharmaceutically acceptable carrier herein may also include other diluents suitable for preparing oral pharmaceutical suspensions. For example, pharmaceutically acceptable additives including stabilizing agents, suspending agents, surface tension modifiers, viscosity modifiers, colorants, preservatives, flavoring agents.

WORKING EXAMPLES

Unless otherwise noted, solvents and reagents were used without purification. 1,2-dichloroethylene (DCE) was dried over 4 Å molecular sieves for 48 h prior to use. Volatile solvents were removed under reduced pressure using a Buchi rotary evaporator. Infrared (IR) spectra were obtained using a Nicolet iS550 FT IR spectrophotometer using a diamond crystal attenuated total reflection (ATR) accessory and reported as wave numbers. Melting points were determined using differential scanning calorimetry (DSC) on a TA Instruments Differential Scanning Calorimeter Model Q100. Thin layer chromatography (TLC) was performed on glass-backed precoated silica gel plates (0.25 mm thick with 60 F254) and were visualized using one or both of the following manners: UV light (254 nm) and staining with $I_2$ impregnated silica. Flash chromatography was performed using the Biotage Isolera One using pre-loaded Silicycle 25 g high performance (14-40 μM) columns. $^1$H nuclear magnetic resonance (NMR) spectra were obtained at 400 MHz as indicated as solutions in CDCl3 with 0.05% v/v tetramethylsilane (TMS) unless indicated otherwise. $^{13}$C-NMR were obtained at 100 MHz as shown in the indicated deuterated solvent. Chemical shifts are reported in parts per million (ppm, δ), and referenced to TMS, and coupling constants are reported in Hertz (Hz). Spectral splitting patterns are designated as s, singlet; d, doublet; t, triplet; q, quartet; quint, quintuplet; sex, sextet; sept, septuplet; m, multiplet; comp, overlapping multiplets of magnetically nonequivalent protons; br, broad; and app, apparent.

General Procedure for Anhydride Formation

Pyridine (1 eq) was added to a stirring solution of the benzoic acid (1 eq) in $CH_2Cl_2$ (2 mL/mmol) at room temperature. Thionyl chloride (0.55 eq) was added to the solution and was allowed to stir at room temperature. The reaction was monitored by TLC (1:1:8 $CH_2Cl_2/Et_2O$/hexanes) and stopped after 2 hours. Diethyl ether (2 mL/mmol) was added to the mixture and vortexed. The slurry was filtered through a silica plug and washed with ether and the filtrate was concentrated under reduced pressure to afford the crude anhydride.

General Procedure for Bis-benzoyloxymethyl Ether Formation

Sulfuric acid (~0.03 eq) was added to a stirring solution of the benzoic anhydride (1 eq) and trioxane (0.55 eq) in DCE (1.22 mL/mmol). The mixture was heated to 60° C. and monitored by TLC (3:3:4 $CH_2Cl_2/Et_2O$/hexanes) unless otherwise indicated. After 3 hours the reaction was removed from heat and a mixture of 1:1 $CH_2Cl_2/H_2O$ (1.5 mL/mmol) was added to the reaction. Ammonium hydroxide (2 drops)

was added to the mixture and was vortexed. The organic phase was collected and concentrated under reduced pressure. The residue was preloaded onto silica and purified by flash chromatography.

12

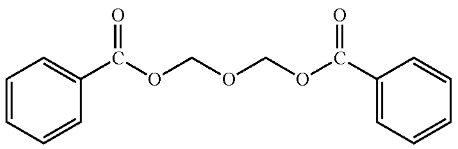

bis-benzoyloxymethyl ether (12). Utilized the following TLC conditions: (1:1:8 $CH_2Cl_2/Et_2O$/hexanes). Isolated 1.31 g (41%) of pure 21a as a white solid. MP: 50° C. $^1$H-NMR (400 MHz) δ 8.02 (app d, J=9.6 Hz, 4H), 7.56 (app t, J=7.2 Hz, 2H), 7.39 (t, J=7.6 Hz, 4H), 5.73 (s, 4H); $^{13}$C-NMR (100 MHz) δ 165.8, 133.5, 130.0, 129.4, 128.5, 87.9; IR (pellet) 1722 (C═O), 1600, 1452, 1426, 1316, 1264, 1196, 1143, 1113, 1090, 1069, 1035, 1025, 1012, 968, 936, 846, 804, 703, 691, 683, 599, 495, 449 $cm^{-2}$.

13

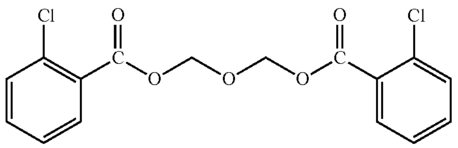

bis-2-chlorobenzoyloxymethyl ether (13). Isolated 477 mg (8%) of pure 13 as a clear oil. $^1$H-NMR (400 MHz) δ 7.86 (m, 2H), 7.47-7.40 (comp, 4H), 7.26 (m, 2H), 5.74 (s, 4H); $^{13}$C-NMR (100 MHz) δ 164.5, 134.2, 133.1, 131.8, 131.2, 128.8, 126.6, 87.9; IR (film) 1731 (C═O), 1591, 1472, 1436, 1291, 1243, 1161, 1108, 1072, 1011, 920, 742, 722, 689, 650, 599, 473 $cm^{-1}$.

14

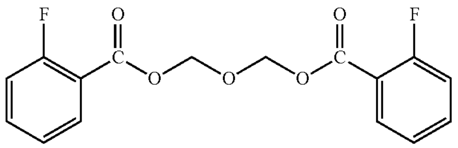

bis-2-flourobenzoyloxymethyl ether (14). Isolated 162 mg (3%) of pure 14 as a clear oil. $^1$H-NMR (400 MHz) δ 7.94 (td, J=1.3, 6.1 Hz, 2H), 7.52 (m, 2H), 7.16 (t, J=5.8 Hz, 2H), 7.10 (dd, J=7.4, 8.6 Hz, 2H), 5.73 (s, 4H); $^{13}$C-NMR (100 MHz) δ 163.3 (d, J=3.8 Hz), 162.2 (d, J=259.7 Hz), 135.1 (d, J=9.1 Hz), 132.3, 124.0 (d, J=4.0 Hz), 117.8 (d, J=9.2 Hz), 117.0 (d, J=22.2 Hz), 87.6; IR (film) 1724 (C═O), 1612, 1488, 1456, 1293, 1246, 1230, 1154, 1116, 1018, 923, 835, 790, 751, 691, 600, 541, 521 $cm^{-1}$.

15

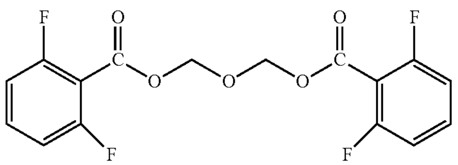

bis-2,6-diflourobenzoyloxymethyl ether (15). Isolated 442 mg (7%) of pure 15 as a white solid. MP: 59° C. $^1$H-NMR (400 MHz) δ 7.45 (m, 2H), 6.97 (t, J=8.4 Hz, 4H), 5.72 (s, 4H); $^{13}$C-NMR (100 MHz) δ 161.0 (dd, J=5.8, 256.6 Hz), 160.6, 133.5 (t, J=10.6 Hz), 112.0 (dd, J=3.0, 18.6 Hz), 110.1 (t, J=16.9 Hz), 87.1; IR (pellet) 1743 (C═O), 1623, 1465, 1284, 1260, 1236, 1150, 1121, 1033, 1008, 962, 923, 884, 829, 799, 772, 690, 580, 525, 512, 489, 405 $cm^{-1}$.

16

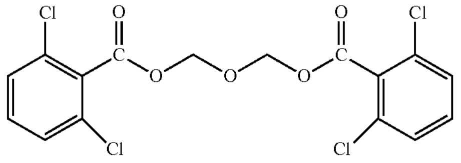

bis-2,6-dichlorobenzoyloxymethyl ether (16). Isolated 264 mg (5%) of pure 16 as a white solid. MP: 61° C. $^1$H-NMR (400 MHz) δ 7.36-7.29 (comp, 6H), 5.75 (s, 4H); $^{13}$C-NMR (500 MHz) δ 163.9, 132.7, 131.9, 131.3, 127.9, 87.4; IR (pellet) 1750 (C═O), 1564, 1432, 1289, 1252, 1195, 1158, 1126, 1096, 1069, 1012, 965, 945, 911, 814, 800, 774, 751, 724, 605 $cm^{-1}$.

17

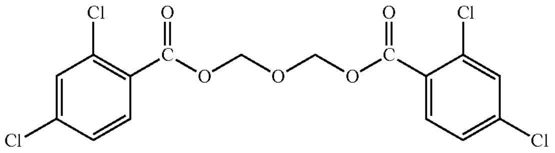

bis-4-chlorobenzoyloxymethyl ether (17). Utilized the following TLC conditions: (2:2:6 $CH_2Cl_2/Et_2O$/hexanes). Isolated 78 mg (1%) of pure 17 as a white solid. MP: 97° C. $^1$H-NMR (400 MHz) δ 7.92 (d, J=8.4 Hz, 4H), 7.36 (d, J=8.4 Hz, 4H), 5.71 (s, 4H); $^{13}$C-NMR (100 MHz) δ 164.8, 140.1, 131.2, 128.8, 127.6, 88.1; IR (pellet) 1727 (C═O), 1713, 1593, 1487, 1457, 1402, 1288, 1267, 1181, 1165, 1090, 1045, 1010, 960, 848, 812, 758, 734, 685, 630, 598, 521, 475, 451, $cm^{-1}$.

18

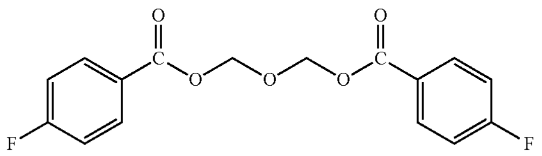

bis-4-flourobenzoyloxymethyl ether (18). Utilized the following TLC conditions: (1:1:8 $CH_2Cl_2/Et_2O$/hexanes). Isolated 698 mg (11%) of pure 18 as a white solid. MP: 77° C. $^1$H-NMR (400 MHz) δ 8.02 (m, 4H), 7.06 (t, J=8.8 Hz, 4H), 5.71 (s, 4H); $^{13}$C-NMR (100 MHz) δ 166.0 (d, J=253.5 Hz), 164.7, 132.4 (d, J=9.4 Hz), 125.5 (d, J=2.9 Hz), 115.6 (d, J=21.9 Hz), 88.0; IR (pellet) 1713 (C═O), 1598, 1505, 1460, 1411, 1267, 1234, 1217, 1196, 1152, 1110, 1095, 1080, 1031, 1011, 954, 923, 860, 852, 821, 792, 763, 688, 585, 542, 499, 485, 465, 423 $cm^{-1}$.

19

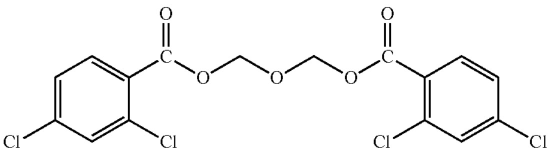

bis-2,4-dichlorobenzoyloxymethyl ether (19). Utilized the following TLC conditions: (1:1:8 $CH_2Cl_2$/$Et_2O$/hexanes). Isolated 3.14 g (28%) of pure 19 as a white solid. MP: 80° C. $^{1}$H-NMR (400 MHz) δ 7.82 (d, J=8.4 Hz, 2H), 7.46 (d, J=2 Hz, 2H), 7.25 (dd, J=2, 8.4 Hz, 2H)l, 5.51 (s, 4H); $^{13}$C-NMR (100 MHz) δ 163.5, 139.1, 135.5, 132.8, 131.2, 127.0, 126.9, 88.2; IR (pellet) 1710 (C═O), 1583, 1469, 1396, 1375, 1292, 1273, 1251, 1161, 1130, 1110, 1074, 1024, 972, 933, 895, 841, 826, 781, 762, 675, 611, 563, 545, 487, 441. 404 $cm^{-1}$.

20

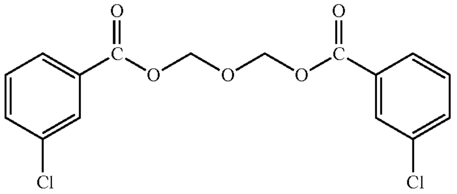

bis-3-chlorobenzoyloxymethyl ether (20). Utilized the following TLC conditions: (1:1:8 $CH_2Cl_2$/$Et_2O$/hexanes). Isolated 680 mg (12%) of pure 20 as a white solid. MP: 65° C. $^{1}$H-NMR (400 MHz) δ 7.96 (t, J=1.6 Hz, 2H), 7.89 (dt, J=1.2, 8.0 Hz, 2H), 7.52 (ddd, J=1.2, 2.0, 8.0 Hz, 2H), 7.33 (t, J=7.6 Hz, 2H), 5.72 (s, 4H); $^{13}$C-NMR (100 MHz) δ 164.5, 134.6, 133.5, 130.9, 129.8, 129.7, 127.9, 88.3; IR (pellet) 1713 (C═O), 1574, 1469, 1420, 1395, 1295, 1255, 1169, 1118, 1101, 1079, 1059, 1014, 945, 897, 890, 809, 749, 737, 672, 658, 575, 497, 464, 424 $cm^{-1}$.

21

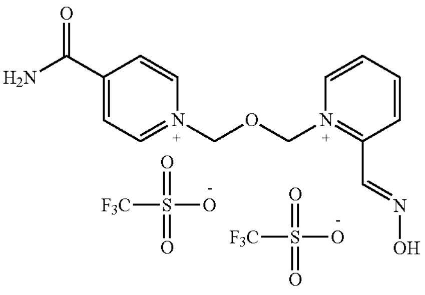

HI-6 bistriflate (21). Trimethylsilyl trifluoromethanesulfonate (0.92 g, 0.75 mL, 4.13 mmol) was added to a 1 dram vial containing linker 10 (250 mg, 0.59 mmol), pyridine-2-aldoxime (72 mg, 0.59 mmol), 2,6-di-tert-butylpyridine (0.53 g, 0.60 mL, 2.65 mmol), and nitromethane (0.25 mL) and the mixture was stirred at 40° C. for 1.5 h, whereupon isonicotinamide (72 mg, 0.59 mmol) was added and the reaction temperature raised to 60° C. and stirred for 16 h. The reaction mixture was then diluted in a mixture (1:1) of MeCN and $H_2O$ (2000 mL) and a sample was run on the HPLC according to the HI-6 calibration curve method. The area response of the sample was determined to be 32.73 mAU, which corresponds to a 101% yield of HI-6 bistriflate (21) by the following relationship:

$$\%\text{ yield} = \frac{D\times(A+N)}{1000\times\varepsilon\times L\times M}$$

where D is the dilution factor of the sample, A is the absorbance (in mAU), N is the Y intercept, e is the molar absorptivity coefficient, L is the moles of linker 10 used in the reaction, and M is the molecular weight of HI-6 DMS (478.50 g/mol).

22

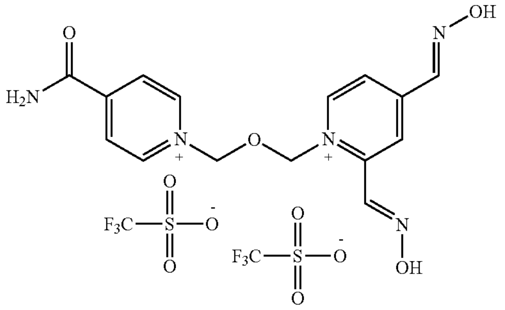

Hlo-7 bistriflate (22). Trifluoromethanesulfonate (0.92 g, 0.75 mL, 4.13 mmol) was added to a 1 dram vial containing linker 10 (250 mg, 0.59 mmol), pyridine-2,4-dialdoxime (97 mg, 0.59 mmol), 2,6-di-tert-butylpyridine (0.53 g, 0.60 mL, 2.65 mmol), and nitromethane (0.25 mL). The mixture was stirred at 40° C. for 1.5 h. Isonicotinamide (72 mg, 0.59 mmol) was added to the mixture and stirred at 60° C. for 16 h. The reaction mixture was then diluted in a mixture (1:1) of MeCN and $H_2O$ (800 mL) and a sample was run on the HPLC according to the Hlo-7 calibration curve method. The area response of the sample was determined to be 20.78 mAU, which corresponds to a 29% yield of Hlo-7 bistriflate (22) by the following relationship:

$$\%\text{ yield} = \frac{D\times(A+N)}{1000\times\varepsilon\times L\times M}$$

where D is the dilution factor of the sample, A is the absorbance (in mAU), N is the Y intercept, ε is the molar absorptivity coefficient, L is the moles of linker 10 used in the reaction, and M is the molecular weight of Hlo-7 DMS (521.52 g/mol).

What is claimed is:

1. A method of forming bis-quaternary pyridinium oximes comprising:

supplying benzoic anhydride having the following structure:

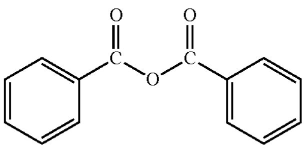 [SMILES: O=C(OC(=O)c1ccccc1)c1ccccc1]

reacting said benzoic anhydride with trioxane to form a dibenzoyloxymethyl ether having the following structure:

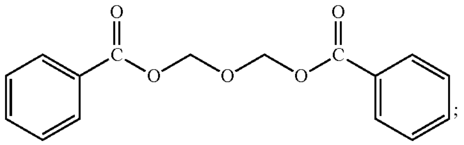 [SMILES: O=C(OCOCOC(=O)c1ccccc1)c1ccccc1]

supplying a substituted pyridine having the following structure:

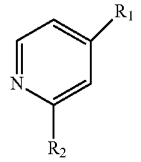

wherein $R_1$ and $R_2$ may be independently selected from the group consisting of consisting of hydrogen, alkyl, —CH═NOH or —$CONH_2$;

combining said dibenzoyloxymethyl ether with said substituted pyridine and forming a salt having the following structure:

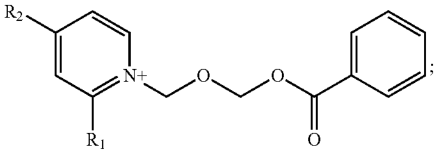

reacting said salt with a substituted pyridine having the following structure:

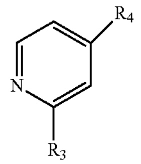

and forming a bis-pyridinium aldoxime salt of the following structure:

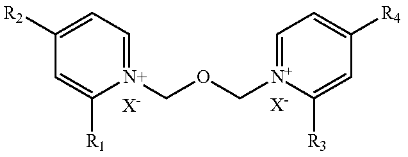

wherein $R_3$ and $R_4$ may be independently selected from the group consisting of consisting of hydrogen, alkyl, —CH═NOH or —$CONH_2$ and $X^-$ comprises Cl— or $^-OSO_2CH_3$.

2. The method of claim 1 wherein $R_1$ is hydrogen, $R_2$ is —CH═NOH, and $R_3$ and $R_4$ are both —CH═NOH, and $X^-$ is $^-OSO_2CH_3$.

3. The method of claim 1 wherein $R_1$=—CH═NOH, $R_2$ is hydrogen, R3 is hydrogen and $R_4$ is —CH═NOH, and $X^-$ is $^-OSO_2CH_3$.

4. The method of claim 1 wherein $R_1$ and $R_3$ are hydrogen, and $R_2$ and $R_4$ are —CH═NOH, and $X^-$ is $^-OSO_2CH_3$.

5. The method of claim 1 wherein said benzoic anhydride contains one or more of an electron withdrawing group (EWG) on the aromatic rings according to the following structure:

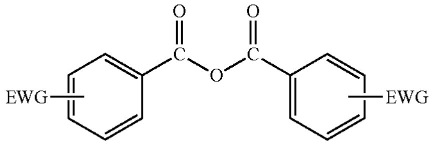

6. The method of claim 1 wherein said bis-pyridinium aldoxime salt:

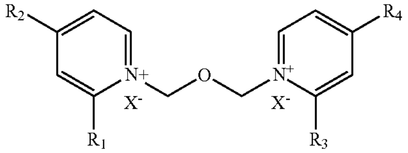

is dispersed in a pharmaceutically acceptable carrier.

7. The method of claim 5 wherein said EWG is an organic trihalide.

8. The method of claim 5 wherein said EWG is a sulfonate.

9. The method of claim 5 wherein said EWG is a nitro group.

10. The method of claim 5 wherein said EWG is an ammonium group.

11. The method of claim 5 wherein said EWG is an aldehyde.

12. The method of claim 5 wherein said EWG is a ketone.

13. The method of claim 5 wherein said EWG is a carboxylic acid.

14. The method of claim 5 wherein said EWG is an acyl chloride.

15. The method of claim 5 wherein said EWG is a benzoate ester.

16. The method of claim 5 wherein said EWG is an amide group.

17. The method of claim 5 wherein said EWG is a halide.

* * * * *